United States Patent [19]

Tsukada et al.

[11] 4,405,989
[45] Sep. 20, 1983

[54] SPECTRAL MONITORING DEVICE FOR BOTH PLASMA ETCHING AND SPUTTERING

[75] Inventors: Tsutomu Tsukada; Katsumi Ukai, both of Tokyo, Japan

[73] Assignee: Anelva Corporation, Tokyo, Japan

[21] Appl. No.: 246,368

[22] Filed: Mar. 23, 1981

[30] Foreign Application Priority Data

Mar. 24, 1980 [JP] Japan .................................. 55-36256

[51] Int. Cl.³ ..................... H01L 21/306; H03K 5/18; G06F 15/46
[52] U.S. Cl. .................................. 364/525; 364/552; 364/468; 156/627; 356/381
[58] Field of Search ............................... 364/488–491, 364/498, 550, 552, 525, 468; 156/626, 627; 356/357, 381, 445

[56] References Cited

U.S. PATENT DOCUMENTS

| | | | |
|---|---|---|---|
| 3,924,113 | 12/1975 | Gill et al. | 364/489 |
| 3,972,617 | 8/1976 | Shibata et al. | 364/498 X |
| 4,126,510 | 11/1978 | Moscony et al. | 156/626 |
| 4,208,240 | 6/1980 | Latos | 156/627 |
| 4,297,676 | 10/1981 | Moriya et al. | 364/490 X |
| 4,308,586 | 12/1981 | Costes | 364/491 X |
| 4,332,833 | 6/1982 | Aspnes et al. | 156/626 X |

OTHER PUBLICATIONS

Digital Methods for Thin Film Analysis Using a Computer-Controlled Auger Spectometer; American Laboratory, vol. 9, No. 3, Mar. 1977, pp. 27–34.

Microcomputerized Facility for On-Line Spectroscopic Plasma Diagnostics; Partlow et al., Optical Engineering, vol. 20, No. 2, Mar./Apr. 1981, pp. 267–270.

In-Situ, Real-Time Thin-Film Refractive Index and Thickness Monitor, Hewig & Jain, IBM Technical Disclosure Bulletin, vol. 25, No. 1, Jun. 1982, pp. 436–438.

Primary Examiner—Edward J. Wise
Attorney, Agent, or Firm—Laff, Whitesel, Conte & Saret

[57] ABSTRACT

In order to monitor the status, such as a decreasing or an increasing thickness, of a layer in response to a single light beam produced from a chamber in which the layer is processed, as by etching or sputtering, by the use of plasma, a monitoring device splits, according to spectral regions, the beam into two components of intensities variable with time and calculates a difference between the intensities, a power of the difference, and a ratio between the intensities. The status is monitored by selecting the difference, power, and ratio. The spectral regions may be 3962 and 3050 Å for an aluminum layer being etched and 3248 and 8115 Å for a copper layer sputter-formed in argon. Preferably, the difference and the power are monitored a predetermined interval of time after start of etch. The ratio is used in combination with a plasma sputtering device.

7 Claims, 4 Drawing Figures

SPECTRAL MONITORING DEVICE FOR BOTH PLASMA ETCHING AND SPUTTERING

BACKGROUND OF THE INVENTION

This invention relates to a spectral monitoring device for use in combination with a layer processing device in which a layer is processed by the use of plasma. The processing may be either of etching and forming, as by sputtering or vapor deposition.

Monitoring devices of various types have been used in monitoring the status of a layer being processed in a chamber of a plasma processing device. Examples are a spectral monitoring device, a crystal thickness monitoring device, and an atomic absorption monitoring device.

Monitoring devices of two latter types are for use in monitoring the rate of growth of the layer. Such a device is incapable of indicating the precise rate of growth. It takes an appreciable time in obtaining the result of monitor. The device is therefore unsuitable on strictly controlling the thickness of the layer being formed. In addition, it has been impossible to use the device in monitoring a layer being etched.

Spectral monitoring devices have been used in monitoring a layer being etched. The devices are operable on various principles.

With conventional spectral monitoring devices, completion of etching is monitored by detecting disappearance of the spectrum of the layer being etched from the light beam resulting from the plasma. The device is advantageous in that the structure is simple. The spectrum being monitored, however, varies also when fluctuation takes place in the source voltage of the high-frequency power surce for use in generating the plasma. Such fluctuation is inevitable because the pressure and the composition of the gas in which the plasma is generated, are variable with the progress of etch. It is therefore difficult to avoid excessive etching of the layer. Furthermore, the device must have a high spectral resolution because spurious spectra may appear adjacent to the spectrum of the layer.

With a spectral monitoring device disclosed in Japanese Unexamined Patent Publication No. Syô 53-50794, namely, No. 50794/78, assigned to the present assignee, completion of etching is detected by calculating a difference between intensities of two beam components included in different spectrum regions. The completion of etching is indicated when the difference is kept constant as regards time. This system is effective to remove the influence of the above-mentioned fluctuation of the source voltage. However, it is not really easy to determine whether the difference becomes constant or not. Therefore, an intricate circuit, such as a microcomputer, is necessary to detect the completion of etching. In addition, the system is hopeless of precise detection because the variations of both spectra tend to be cancelled relative to each other by calculation of the difference. The spectra are derived through different windows attached to the chamber of the etching device. Therefore, each spectrum is subjected to an influence of contamination of each of the windows and is individually changed in its intensity.

SUMMARY OF THE INVENTION

It is therefore an object of this invention to provide a monitoring device which is applicable to both of plasma etching and layer forming devices, such as plasma sputtering or plasma enhanced chemical vapor deposition devices.

It is another object of this invention to provide a monitoring device of the type described, which is capable of precisely and rapidly detecting completion of etching.

It is still another object of this invention to provide a monitoring device of the type described, which is simple in structure and need not use a microcomputer and a monochrometer having a high resolution.

It is yet another object of this invention to provide a monitoring device of the type described, which is not substantially affected by contamination of a window attached to a chamber of each of the plasma sputtering and etching devices.

It is another object of this invention to provide a monitoring device of the type described, wherein a deposit rate of growth is directly monitored when the monitoring device is coupled to a layer forming device.

A monitoring device to which this invention is applicable is responsive to a single light beam produced from a chamber of a layer processing device, in which chamber a layer is processed by plasma into gradual changes in status, for monitoring the instantaneous status of the layer. The beam including a first component in a first spectrum region and a second component in a second spectrum region different from said first spectrum region. According to this invention, the monitoring device comprises beam splitting means for splitting the beam according to the first and the second spectrum regions into first and second split beams comprising the first and the second components and having first and second intensities which vary with instantaneous changes in status, respectively, detecting means responsive to the first and the second split beams for detecting the first and the second variable intensities to produce a first electrial signal having a first level representative of the first variable intensity and a second electrical signal having a second level representative of the second variable intensity, respectively, first calculating means responsive to the first and the second electrical signals for calculating a difference between the first and the second levels to produce a different signal having a difference level representative of the difference, second calculating means responsive to the difference signal for calculating a power of the difference to produce a power signal having a power level representative of the power, third calculating means responsive to the first and the second electrical signals for calculating a ratio of the first variable level to the second variable level to produce a ratio signal having a ratio level representative of the ratio, and processing means coupled to the first through the third calculating means for processing the level of a selected one of the difference, the power, and the ratio signals to monitor the instantaneous and gradual changes in the status of the layer.

DESCRIPTION OF THE PREFERRED EMBODIMENTS

Figure 1:
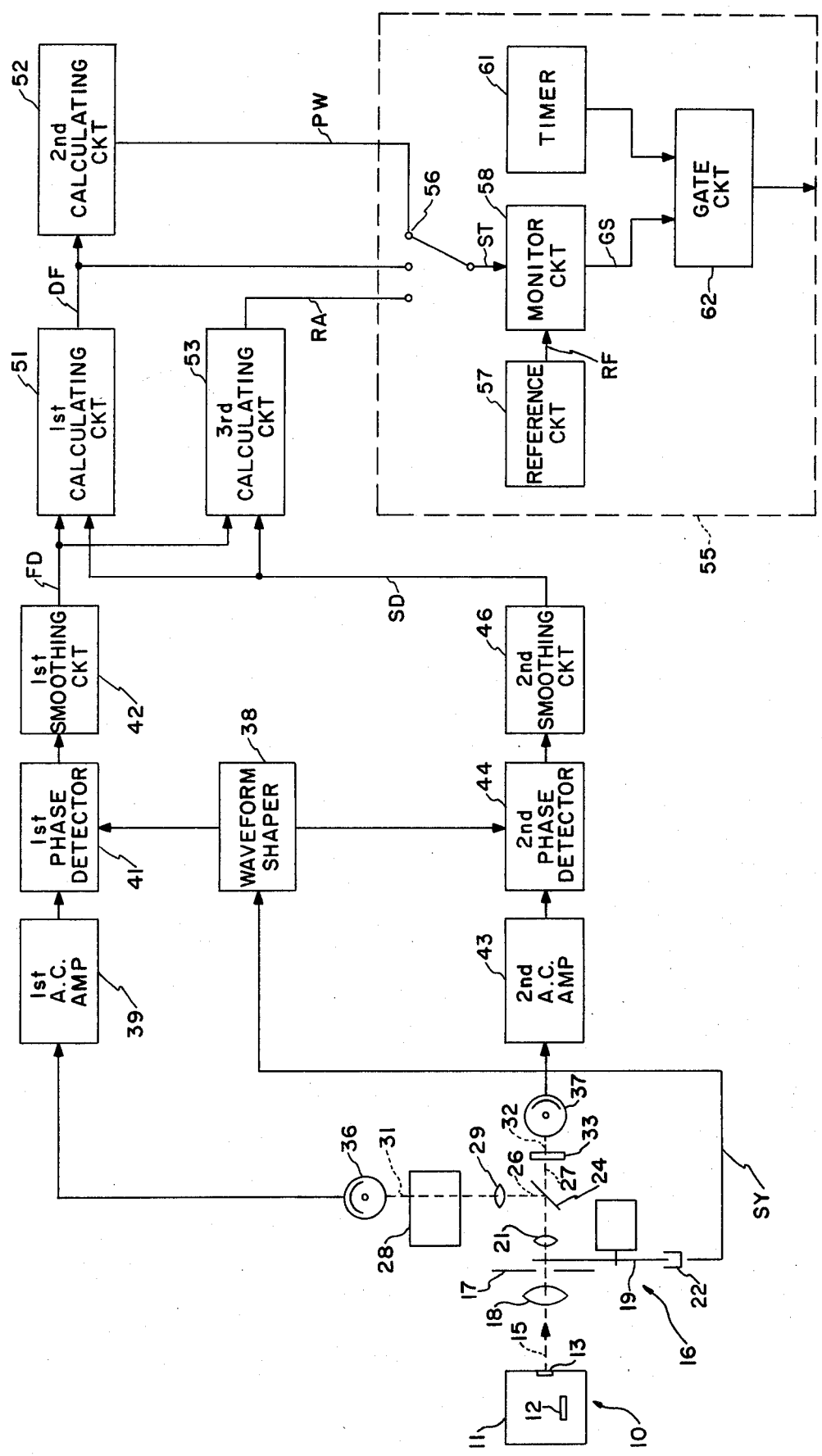
FIG. 1 is a block diagram of a monitoring device according to a preferred embodiment of this invention.

Referring to FIG. 1, a monitoring device according to a preferred embodiment of this invention is for use in combination with a layer processing device 10. The layer processing device may be either a layer etching device or a layer forming device, such as a sputtering device, and comprises a chamber 11 in which a layer 12 is processed by plasma into gradual status. The chamber 11 is provided with a single window 13. The gradual changes in status appears as a gradual variation of a thickness of the layer 12. The monitoring device 10 is for monitoring and detecting a completion of the etching away or the growth of the layer 12 to a predetermined thickness when the layer etching and the layer forming devices are coupled to the monitoring device, respectively. A light appears within the chamber 11 during the processing of the layer 12. A light beam 15 is taken out through the window 13. The light beam 15 includes a first component in a first spectrum region and a second component in a second spectrum region different from the first spectrum region.

In FIG. 1, the light beam 15 is received by an optical system 16 of the monitoring device according to the embodiment. In the optical system 16, the light beam 15 is focused at a slit 17 through a focusing or convex lens 18. The focused light beam 15 is chopped at a predetermined interval of, for example, 1/200 second by an optical chopper 19 arranged in the rear of the slit 17 and is incident onto a lens 21 to derive a parallel and chopped beam. The chopper 19 is optically coupled to an optical sensor 22 to produce a synchronizing signal SY appearing at the predetermined interval. The chopped beam is separated by a translucent mirror 24 into first and second partial beams 26 and 27 each of which includes the first and the second components. The first and the second partial beams 26 and 27 are reflected by and transmitted through the mirror 24, respectively. The first partial beam 26 is supplied to a monochrometer 28 through a lens 29 to derive a first split beam 31 comprising the first component. On the other hand, a second split beam 32 which comprises the second components is produced through an optical filter 33. The first and the second split beams 31 and 32 have first and second variable intensities, respectively.

Thus, the optical system 16 serves to split the light beam 15 into the first and the second split beams 31 and 32.

Further referring to FIG. 1, the monitoring device comprises first and second photomultipliers 36 and 37 responsive to the first and second split beams 31 and 32 and a wave-form shaper 38 responsive to the synchronizing signal SY. The first photomultiplier 36 converts the first split beam 31 to a first a.c. electrical signal having a frequency equal to a reciprocal of the predetermined interval. The first a.c. electrical signal is supplied through a first a.c. amplifier 39 and then to a first phase detector 41 to which the synchronizing signal SY is sent through the wave-form shaper 38. The first phase detector 41 carries out coherent detection to convert the first a.c. signal to a first d.c. electrical signal. The first d.c. electrical signal is produced through a first smoothing circuit 42 as a first detection signal FD. The first detection signal FD has a first variable level representation of the first variable intensity.

The second photomultiplier 37 converts the second split beam 32 to a second a.c. electric signal having a frequency equal to that of the first a.c. electrical signal. The second a.c. electric signal is supplied through a second a.c. amplifier 43 to a second phase detector 44. Similarly to the first phase detector 41, the second phase detector 44 converts the second a.c. electric signal to a second d.c. electrical signal. The second d.c. electric signal is produced through a second smoothing circuit 46 as a second detection signal SD. The second detection signal SD has a second variable level representative of the second variable intensity.

Referring to FIG. 1 again, the monitoring device further comprises a difference calculating circuit 51 responsive to the first and the second detection signals FD and SD for calculating a difference between the first and the second variable levels. The difference calculating circuit 51 produces a difference signal DF having a difference level representative of the difference. Supplied with the difference signal DF, a power calculating circuit 52 calculates a power of the difference to produce a power signal PW having a power level representative of the power. The illustrated power calculating circuit 52 is formed by a multiplier calculating a square of the difference. Herein, the difference and the power calculating circuits 51 and 52 will be called first and second calculating circuits, respectively, and are put into operation when the etching device is located as the layer processing device 10, as will become clear as the description proceeds. The power may be a cube, a biquadrate, or the like.

Supplied with the first and the second detection signals FD and SD, a third calculating circuit 53 calculates a ratio of the first variable level to the second variable level to produce a ratio signal RA having a ratio level representative of the ratio. The third calculating circuit 53 is available on monitoring the layer forming device, such as sputtering device, as will be described later.

In FIG. 1, a processing circuit 55 is coupled to the first through the third calculating circuits 51 through 53 for processing the level of a selected one of the difference, the power, and the ratio signals DF, PW, and RA to monitor the gradual status of the layer 12.

More particularly, the processing circuit 55 comprises a selector 56 coupled to the first through the third calculating circuits 51 through 53. When the layer 12 is etched, the selector 56 selects, as a selected level signal ST, the difference signal DF or the power signal PW. The selector 56 selects, as the selected level signal ST, the ratio signal RA when the layer 12 is formed by the layer processing device 10. A reference signal circuit 57 in the processing circuit 55 produces a reference signal RF having a reference level. The reference signal RF may be selectively produced from the reference signal circuit 57 in accordance with the selected level signal ST. Responsive to the selected level signal ST and the reference signal RF, a monitor circuit 58 monitors the level of the selected level signal ST with reference to the reference signal RF to produce a status signal GS representative of the gradual status of the layer 12 when the monitored level is substantially coincident with the reference level. In the example being illustrated, the processing circuit 55 further comprises a timer circuit 61 for timing a predetermined duration of, for example, five minutes from start of processing the layer 12 to produce a timing signal TM and a gate circuit 62 coupled to the timing circuit 61 and the monitor circuit 58. The gate circuit 62 passes through the status signal GS only when enabled by the timing signal TM. In other words, the gate circuit 62 suppresses production of the status signal GS until appearance of the timing signal TM. This operation is very effective to avoid malfunction of the processing circuit 55, as become clear soon. In addition, all elements of the processing circuit 55 are simple and of low prices. Therefore, an intricate circuit, such as a microcomputer, need not be used in the processing circuit 55. For the monochrometer 26, high resolution and high spectral sensitivity are not indispensable in this monitoring device because comparison is relatively carried out between two components derived from a single light beam. Therefore, the monochrometer 26 may be of a small size or be replaced by a simple band pass filter.

Figure 2:
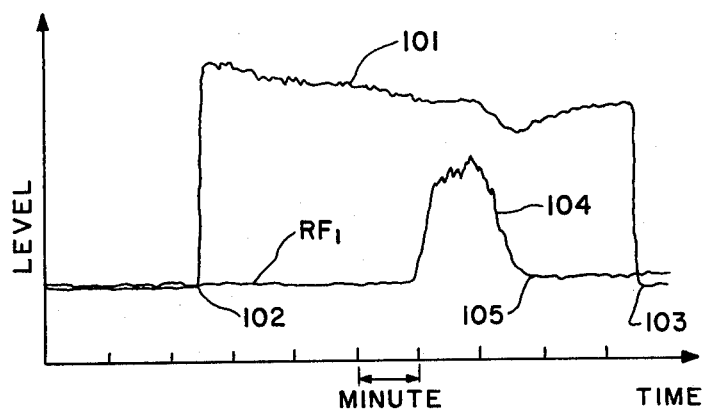
FIG. 2 is a graphical representation for describing operation carried out when a layer processing circuit is used to etch an aluminum layer.

Referring to FIG. 1 again and FIG. 2 afresh, it is assumed that an aluminum layer is used as the layer 12 and is etched by the layer processing device 10. Preferably, the first and the second spectrum regions should comprise 3962 and 3050 angstroms. The first component of 3962 angstrom results from an emission spectrum of aluminum. The monochrometer 28 is for deriving the first component of 3962 angstrom as the first split beam 31 having the first variable intensity. In FIG. 2, the abscissa and the ordinate represent time (minute) and either the first variable level representative of the first variable intensity or the power level of the power signal PW produced from the second calculating circuit 52, respectively. As shown by a curve 101 in FIG. 2, the first variable intensity rapidly rises from a reference level at a start point 102 of etching. The intensity returns to the reference level at an instant 103. The instant 103 has to be coincident with that of completion of etching. It has, however, been found that the instant 103 is not coincident with that of completion. This is because the curve 101 is affected by any emission spectrum of a background other than aluminum. Accordingly, a spectral intensity of the background is monitored to detect completion of etching in the monitoring device illustrated in FIG. 1. More particularly, use is made of the optical filter 33 deriving the second component of 3050 angstrom which results from the background. The second component of 3050 angstrom is produced from the optical filter 33 as the second split beam 32.

The processing circuit 55 is supplied with the first and the second detection signals FD and SD resulting from the first and second components of 3962 and 3050 angstroms, respectively. The first and the second detection signals FD and SD have the first and the second variable levels, as described before. In the processing circuit 55, the selector 56 is coupled to the second or power calculating circuit 52 responsive to the difference signal DF produced from the first calculating circuit 51. The second calculating circuit 52 calculates the square of the difference between the first and the second levels to produce the power signal PW having the power level. The power signal PW is sent to the monitor circuit 58 as the selected level signal ST. As shown by a curve 104 in FIG. 2, the power level rises from a reference level $RF_1$ after the starting point 102 and returns at a prior instant 105 to the reference level $RF_1$ before the instant 103. According to the experimental studies, the prior instant 105 was completely coincident with the instant of completion of etching. It is, therefore, possible to detect the completion of etching by monitoring the prior instant 105.

More particularly, the monitor circuit 58 produces the status signal GS when the level of the selected level signal ST, namely, power signal PW is equal to that of the reference signal RF. This means that the status signal GS is produced not only after the power level returns to the reference level $RF_1$ but also before the power level rises from the reference level $RF_1$. The timer 61 suppresses production of the status signal GS until the power level rises up. For this purpose, the timer 61 times the predetermined duration of five minutes from the start point 102. Thus, the completion of etching is indicated by the status signal GS.

Figure 3:
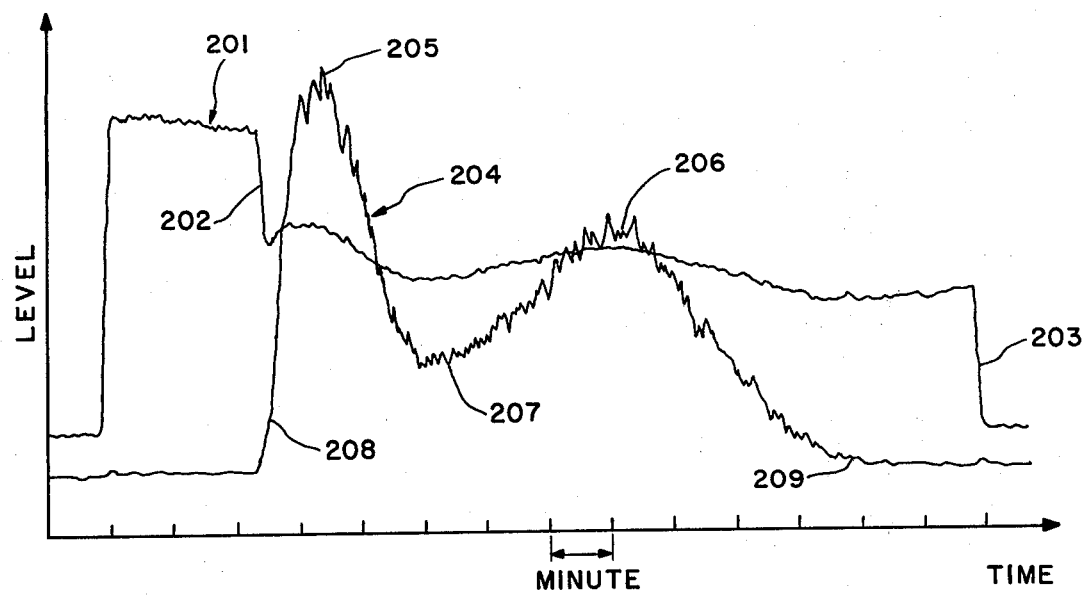
FIG. 3 is a similar graphical representation for describing operation carried out when an alloy of aluminum-silicon is etched by the layer processing device.

Referring to FIG. 3, a curve 201 shows a variation of the intensity of the spectrum of aluminum appearing when an alloy of aluminum-silicon is etched by the layer processing device 10. The device 100 is driven by a power source (not shown) having a source voltage of a high frequency. The alloy comprised 2.0% by weight of silicon, the balance being aluminum. The spectrum of aluminum is specified by the first component of 3962 angstrom, like in FIG. 2. The curve 201 locally has a downwardly decreasing portion 202 and a trailing edge portion 203. The downwardly decreasing portion 202 results from fluctuation of the source voltage. When the curve 201 alone is monitored by the use of a microcomputer or the like, it is likely that the downwardly decreasing portion 202 is erroneously regarded as completion of etching. As is the case with FIG. 2, the square of the difference between the first and the second levels is calculated by the use of the first and the second calculating circuits 51 and 52. In FIG. 3, a curve 204 shows a level variation of the square of the difference and has two peaks 205 and 206, a notch 207 interposed therebetween, leading edge or build-up portion 208, and a gradually building down portion 209. The building down portion 209 specifies completion of etching of the alloy. The notch 207 has a level higher than the building down portion 209 and is, therefore, distinguished from the building down portion 209 by the use of the processing circuit 55 illustrated in FIG. 1. In addition, the curve 204 is not affected by the intermediate decreased portion 202 of the curve 201. Therefore, no malfunction takes place.

Figure 4:
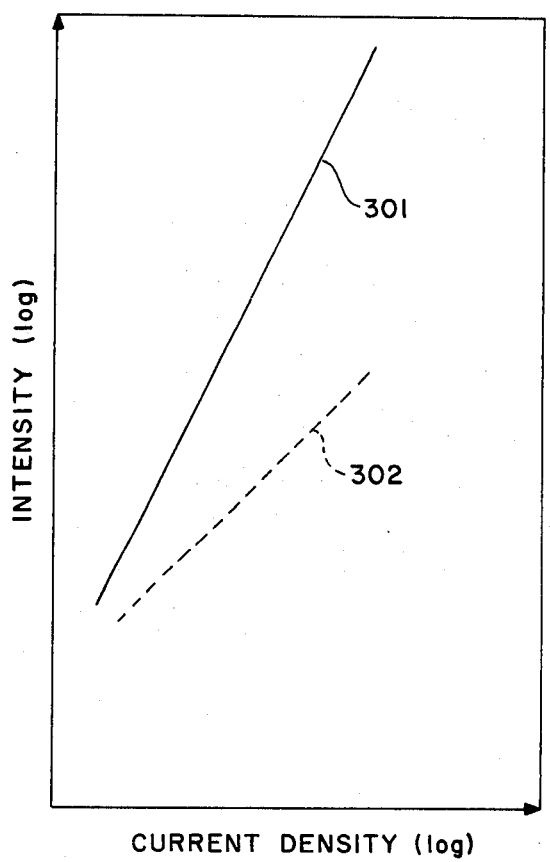
FIG. 4 is a graph for describing an operation carried out when a copper layer is formed by the layer processing device.

Referring to FIG. 4, a case will be described where the monitoring device illustrated in FIG. 1 is for use in combination with the layer processing device 10 for forming a layer 12 of copper by sputtering. The layer processing device 10 is of a magnetron type and comprises a chamber 11 filled with a gas consisting essentially of argon. A target (not shown) is located within the chamber 11 and a target current flows through the target during sputtering. The first and the second spectrum regions comprise 3248 and 8115 angstroms which result from emission spectra of excited atoms of copper and argon, respectively, and which are produced from the monochrometer 28 and the optical filter 33 as the first and the second components, respectively. The first and the second components have first and second variable intensities, as described with reference to FIG. 1.

In FIG. 4, the abscissa and the ordinate represent density of the target current and each intensity of the first and the second components, respectively, each of the target current and the intensity being designated on a logarithmic scale. A curve 301 shows a density versus intensity characteristic of the first component resulting from the copper atoms. The spectral intensity of the copper atoms may be assumed to be proportional to a product of the target current density and density of copper atoms drifting in the chamber 11. Another curve 302 shows a density versus intensity characteristic of the second component resulting from argon atoms. It is readily understood from the curve 302 that a spectral intensity of argon atoms is proportional to the target current density. This means that the density of the copper atoms drifting in the chamber is represented by dividing the spectral intensity of copper atoms by the spectral intensity of argon atoms. Now, the density of the copper atoms is proportional to the deposit rate of the copper layer. The thickness of the copper layer being formed is readily calculated from the deposit rate.

Taking the above into consideration, the selector 56 selects the ratio signal RA as the selected signal level and the monitor circuit 58 produces the status signal GS to represent the thickness of the copper layer being formed. Thus, the thickness is monitored as the gradual status by the monitoring device.

While this invention has thus far been described in conjunction with a preferred embodiment thereof, it will be readily possible for those skilled in the art to put this invention into practice in various manners. For example, the optical chopper 19 and the optical sensor 22 may be removed from the monitoring device. Instead of the translucent mirror 24, use may be made of a rotation mirror of a sector configuration. Light emitting diodes may be substituted for the photomultipliers 36 and 37. The light beam 15 may be introduced to the monitoring device through an optical fiber.

What is claimed is:

1. A monitoring device operated responsive to a single light beam which is produced in a chamber of a layer processing device, said chamber including a source of plasma which proceeses said layer in gradual status changes, said device monitoring the instantaneous changes in status of said layer, said gradual status changes resulting from gradual variations of thickness of said layer, said light beam including a first component in a first spectrum region and a second component in a second spectrum region which is different from said first spectrum region, said monitoring device comprising:
   beam splitting merans for splitting said beam according to said first and said second spectrum regions into first and second split beams comprising said first and said second components and having first and second variable intensities, respectively;
   detecting means responsive to said first and said second split beams for detecting said first and said second variable intensities to produce a first electrical signal having a first variable level which is representative of said first variable intensity and a second electrical signal having a second variable level which is representative of said second variable intensity, respectively whereby the instantaneous levels of each of said electrical signals corresponds to the then instantaneous intensities of the respective components;
   first calculating means responsive to said first and said second electrical signals for calculating an instantaneous difference between said first and said second variable levels to produce a different signal having a difference level which is representative of said difference;
   second calculating means responsive to said difference signal for calculating a power of said difference to produce a power signal having a power level which is representative of said power;
   third calculating means responsive to said first and said second electrical signals for calculating a ratio of said first variable level to said second variable level to produce a ratio signal having a ratio level which is representative of said ratio; and processing means coupled to said first through said third calculating means and operated responsive to the level of a selected one of said difference, said power, and said ratio signals to monitor the instantaneous and gradual changes in the status of said layer.

2. A monitoring device as claimed in claim 1, wherein said processing means comprises:
   selecting means coupled to said first through said third calculating means for selecting, as said selected signal, either of said difference and said power signals and said ratio signal when said layer is processed to be etched and formed, respectively;
   reference signal producing means for producing a reference signal having a reference level; and
   monitoring means responsive to said selected signal and said reference signal for monitoring the level of said selected signal with reference to said reference level to produce a status signal representative of the gradual status of said layer when the monitored level is substantially coincident with said reference level.

3. A monitoring device as claimed in claim 2, wherein said processing means further comprises:
   timing means for timing a predetermined duration from start of processing said layer to produce a timing signal; and
   means coupled to said timing means and said monitoring means for suppressing production of said status signal until appearance of said timing signal.

4. A monitoring device as claimed in claim 3, said layer being an aluminum layer and being processed to be etched, said first and said second spectrum regions comprising 3962 and 3050 angstroms, respectively, wherein:
   said selecting means selects said power signal as said selected signal;
   said monitoring means producing the status signal to indicate completion of etching away of said aluminum layer.

5. A monitoring device as claimed in claim 2, said layer being a copper layer and being processed to be formed, said chamber being filled with a gas consisting essentially of argon, said first and said second spectrum regions comprising 3248 and 8115 angstroms, respectively, wherein:
   said selecting means selects said ratio signal as said selected signal;
   said monitoring means producing the status signal to represent the thickness of said copper layer being formed.

6. A monitoring device as claimed in any one of claims 1, 2, 3, 4, and 5, wherein said beam splitting means comprises:
   a translucent mirror for separating said beam into first and second partial beams, each of which includes said first and said second components;
   a monochrometer responsive to said first partial beam for producing said first split beam; and
   an optical filter for filtering said second partial beam to produce said second split beam.

7. A monitoring device as claimed in any one of claims 1, 2, 3, 4, and 5, wherein said beam splitting means comprises:

- optical chopping means for chopping said beam at every predetermined period into a chopped beam including said first and said second components;
- a translucent mirror for separating said chopping beam into first and second partial chopped beams, each of which includes said first and said second components;
- first optical means responsive to said first partial chopped beams for producing said first split beam;
- second optical means responsive to said second partial chopped beam for deriving said second split beam; and
- coupling means coupled to said chopping means for producing a synchronizing signal at every predetermined period;

said detecting means comprising:

- first converting means for converting said first split beam to a first a.c. electric signal having a frequency equal to a reciprocal of said predetermined period;
- first d.c. converting means responsive to said first a.c. electric signal and said synchronizing signal for converting said first a.c. electric signal to a first d.c. electric to produce said first d.c. electric signal as said first electric signal;
- second converting means for converting said second split beam to a second a.c. electric signal having a frequency equal to a reciprocal of said predetermined period; and
- second d.c. converting means responsive to said second a.c. electric signal and said synchronizing signal for converting said second a.c. electric signal to a second d.c. electric signal to produce said second d.c. electric signal as said second electric signal.

* * * * *